United States Patent [19]

Ling et al.

[11] Patent Number: 4,517,181
[45] Date of Patent: May 14, 1985

[54] MAMMALIAN PGRF

[75] Inventors: Nicholas C. Ling, San Diego; Frederick S. Esch, Oceanside; Peter Bohlen, Encinitas; Paul E. Brazeau, Jr., San Diego; Roger C. L. Guillemin, La Jolla, all of Calif.

[73] Assignee: The Salk Institute for Biological Studies, San Diego, Calif.

[21] Appl. No.: 418,248

[22] Filed: Sep. 15, 1982

[51] Int. Cl.$^3$ ..................... A61K 37/02; C07C 103/52
[52] U.S. Cl. ................................. 514/12; 260/112.5 R
[58] Field of Search .................. 424/177; 260/112.5 R

[56] References Cited

U.S. PATENT DOCUMENTS 4,201,840  5/1980  Campbell et al. .
4,344,938  8/1982  Sedlacek et al. .
4,350,761  9/1982  Yamamoto .

OTHER PUBLICATIONS

Ling et al., *Proc. Natl. Acad. Sci. USA*, 73, No. 9, pp. 3308–3310 (1976).
Sayers, *ACTH and Related Peptides*, 297, 220–241 (1977).
Tregear, *Biochemistry*, 16, No. 13, 2817–2823 (1977).
Li et al., *J. Am. Chem. Soc.*, 92:26 (1970), pp. 7608–7609.
Veber et al., *Biochem. & Biophys. Res. Commun.*, 45, No. 1 (1971), pp. 235–239.
Frohman et al., *Clin. Invest.*, 65 (1980), pp. 43–54.
Esch et al., *Biochemical and Biophysical Research Communications*, vol. 109, No. 1, 152–158 (1982).
Esch et al., *The Journal of Biological Chemistry*, vol. 258, No. 3, 1806–1812 (1983).
Vance et al., *J. of Clinical Endocrinology and Metabolism*, vol. 58, 1984, pp. 838–843.
Borges et al., *J. of Clinical Endocrinology and Metabolism*, vol. 59, No. 1, 1984, pp. 1–6.
Scanes et al., *Life Sciences*, vol. 34, 1984, pp. 1127–1134.
Peter et al., *Neuroendocrinology*, In press, submitted 8/83.

*Primary Examiner*—Delbert R. Phillips
*Assistant Examiner*—F. T. Moezie
*Attorney, Agent, or Firm*—Fitch, Even, Tabin & Flannery

[57] ABSTRACT

PGRF has been synthesized. The invention provides synthetic peptides which are extremely potent in stimulating the release of pituitary GH in mammals and which have the formula:

H~Tyr~Ala~Asp~Ala~Ile~Phe~Thr~Asn~Ser~Tyr~
Arg~Lys~Val~Leu~Gly~Gln~Leu~Ser~Ala~Arg~Lys~
Leu~Leu~Gln~Asp~Ile~Met~Ser~Arg~Gln~Gln~Gly~
Glu~$R_{34}$~Asn~Gln~Glu~$R_{38}$~Gly~$R_{40}$~$R_{41}$~R wherein R is OH or $NH_2$, $R_{34}$ is Ser or Ala, $R_{38}$ is Arg or Ser, $R_{40}$ is Ala or Arg and $R_{41}$ is Arg, Arg-Ala, Arg-Ala-Arg, Arg-Ala-Arg-Leu or des-$R_{41}$. These peptides or biologically active fragments thereof, or analogs thereof having well-known substitutions and/or additions, as well as nontoxic salts of any of the foregoing, may be administered therapeutically to mammals, including humans, and may be used diagnostically.

20 Claims, No Drawings

MAMMALIAN PGRF

This invention was made with Government support under Grants AM-18811 and HD-09690 awarded by the National Institutes of Health. The Government has certain rights in this invention.

This application claims priority from International Application No. PCT/US82/00812 filed June 16, 1982 under the provisions of 35 U.S.C. 363 and now abandoned, of which this application is a continuation-in-part, as provided for in 35 U.S.C. 365(c).

The present invention relates to a peptide having influence on the function of the pituitary gland in humans and other mammals. In particular, the present invention is directed to a peptide which promotes the release of growth hormone by the pituitary gland.

BACKGROUND OF THE INVENTION

Since the early 1950's, physiologists and clinicians have recognized that the hypothalamus of the brain controls all the secretory functions of the adenohypophysis. This control is neurohumoral, with specialized neurosecretory neurons in the hypothalamus producing special polypeptides, the effect and role of each of which is to trigger acutely and chronically the secretion of each pituitary hormone. To this day, a hypothalamic releasing factor has been characterized for the pituitary hormones thyrotropin and prolactin (the tripeptide TRF), for the pituitary gonadotropins luteinizing hormone and follicle stimulating hormone (the decapeptide LRF, LH-RH, GnRH or Gn-RF) and for the pituitary hormones β-endorphin and adrenocorticotropin (the 41-amino acid polypeptide CRF). In addition, an inhibitory factor has been characterized: hypothalamic somatostatin inhibits, at the pituitary level, the secretion of growth hormone. Each of these hypothalamic releasing factors and somatostatin have been reproduced by total synthesis, and many analogs of the native structures have been synthesized, some with far greater activity than the natural compounds.

To this day, a corresponding hypothalamic releasing factor for the pituitary growth hormone or somatotropin has not been characterized, even though there has been extensive physiological and clinical evidence for its existence. One of the major problems in the isolation and characterization of the hypothalamic growth hormone releasing factor (hereinafter GRF) is that the active peptide appears to be present in each hypothalamic fragment in infinitesimal amounts which we believe to be of the order of 50–150 femtomoles. This is far less than anything ever calculated for the other hypothalamic releasing factors. In keeping with this statement is the corollary that hypothalamic GRF is of extremely high potency.

Another major problem in the isolation of hypothalamic GRF has been the presence in hypothalamic extracts of very large amounts of somatostatin which of course prevent or would give aberrant results in any attempted bioassay. Over the last few years, several laboratories have claimed to have isolated and characterized the hypothalamic GRF; all these claims were dealing with artifacts as recognized later by the authors (Schally, A. V. S. et al. *J. Biol. Chem.* 246, 6647, 1971; Veber D. F. et al., *Biochem. Biophys. Res. Commun.* 45, 235, 1971). Such incorrect claims can be explained in part, by the difficulty of the bioassays involved in assessing release of growth hormone.

SUMMARY OF THE INVENTION

A 44-residue polypeptide has been isolated from a human islet cell tumor, purified, characterized, synthesized and tested which promotes the release of growth hormone(GH) by the pituitary. This peptide has the sequence:

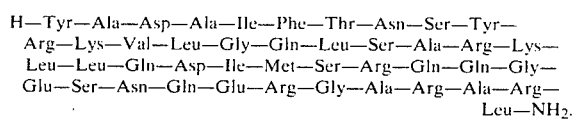

It is believed to be and is hereinafter referred to as PGRF (for human pancreatic GRF) and will also be termed somatocrinin. It has also been determined that the sequence of human hypothalamic GRF is identical to that of human pancreatic GRF (PNAS, Prant, USA, Vol. 81, 1984, pp 4302–4306). Two other highly purified peptides were also isolated along therewith which exhibit GH-releasing activity and which are PGRF(1–37) free acid and PGRF(1–40) free acid.

Pharmaceutical compositions in accordance with the invention include PGRF, an analog or biologically active fragments thereof, or a nontoxic salt thereof dispersed in a pharmaceutically acceptable liquid or solid carrier. Such pharmaceutical compositions can be used in clinical medicine, both human and veterinary, in acute or chronic administration for diagnostic or therapeutic purposes.

DETAILED DESCRIPTION OF PREFERRED EMBODIMENTS

The nomenclature used to define the peptides is that specified by Schroder & Lubke, "The Peptides", Academic Press (1965), wherein in accordance with conventional representation the amino group at the N-terminal appears to the left and the carboxyl group at the C-terminal to the right. Where the amino acid residue has isomeric forms, it is the L-form of the amino acid that is represented unless otherwise expressly indicated.

The invention provides synthetic PGRF peptides having the following formula:

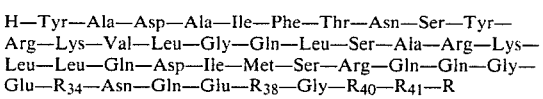

wherein R is OH or $NH_2$, $R_{34}$ is Ser or Ala, $R_{38}$ is Arg or Ser, $R_{40}$ is Ala or Arg, and $R_{41}$ is Arg, Arg-Ala, Arg-Ala-Arg, Arg-Ala-Arg-Leu or des-$R_{41}$.

The peptides are synthesized by a suitable method, such as by exclusively solid-phase techniques, by partial solid-phase techniques, by fragment condensation, by classical solution couplings, or by the employment of recently developed recombinant DNA techniques. For example, the techniques of exclusively solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to such syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Also considered to be within the scope of the present invention are intermediates of the formula:

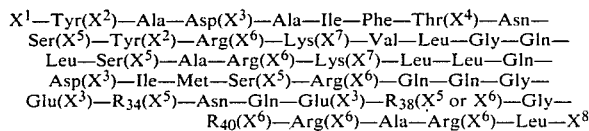

wherein: $X^1$ is either hydrogen or an α-amino protecting group. The α-amino protecting groups contemplated by $X^1$ are those known to be useful in the art of step-wise synthesis of polypeptides. Among the classes of α-amino protecting groups covered by $X^1$ are (1) acyl-type protecting groups, such as formyl, trifluoroacetyl, phthalyl, toluenesulfonyl(Tos), benzensulfonyl, nitrophenylsulfenyl, tritylsulfenyl, o-nitrophenoxyacetyl, chloroacetyl, acetyl, and γ-chlorobutyryl; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethyloxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; (5) thiourethan-type protecting groups, such as phenylthiocarbonyl; (6) alkyl-type protecting groups, such as triphenylmethyl (trityl), benzyl; (7) trialkylsilane groups, such as trimethylsilane. The preferred α-amino protecting group is BOC.

$X^2$ is a protecting group for the phenolic hydroxyl group of Tyr selected from the group consisting of tetrahydropyranyl, tert-butyl, trityl, Bzl, CBZ, 4Br-CBZ and 2,6-dichlorobenzyl. The preferred protecting group is 2,6-dichlorobenzyl. $X^2$ can be hydrogen which means that there is no protecting group on the hydroxyl group.

$X^3$ is hydrogen or an ester-forming protecting group for the carboxyl group of Asp or Glu and is selected from the group consisting of Bzl, 2,6-dichlorobenzyl, methyl and ethyl.

$X^4$ and $X^5$ are protecting groups for the hydroxyl group of Thr and Ser and are selected from the group consisting of acetyl, benzoyl, tert-butyl, trityl, tetrahydropyranyl, Bzl, 2,6-dichlorobenzyl and CBZ. The preferred protecting group is Bzl. $X^4$ and/or $X^5$ can be hydrogen, which means there is no protecting group on the hydroxyl group.

$X^6$ is a protecting group for the guanidino group of Arg selected from the group consisting of nitro, Tos, CBZ, adamantyloxycarbonyl, and BOC, or is hydrogen;

$X^7$ is hydrogen or a protecting group for the side chain amino substituent of Lys. Illustrative of suitable side chain amino protecting groups are 2-chlorobenzyloxycarbonyl (2-Cl—Z), Tos, CBZ, t-amyloxycarbonyl and BOC.

The selection of a side chain amino protecting group is not critical except that it must be one which is not removed during deprotection of the α-amino groups during the synthesis. Hence, the α-amino protecting group and the side chain amino protecting group cannot be the same.

$X^8$ is selected from the class consisting of OH, OCH$_3$, esters, amides, hydrazides, —O—CH$_2$-resin support and —NH-resin support, with the groups other than OH and amides being broadly considered as protecting groups.

In the formula for the intermediate, at least one of $X^1$, $X^2$, $X^3$, $X^4$, $X^5$, $X^6$, $X^7$, and $X^8$ is a protecting group.

In selecting a particular side chain protecting group to be used in the synthesis of the peptides, the following rules are followed: (a) the protecting group must be stable to the reagent and under the reaction conditions selected for removing the α-amino protecting group at each step of the synthesis, (b) the protecting group must retain its protecting properties and not be split off under coupling conditions, and (c) the side chain protecting group must be removable, upon the completion of the synthesis containing the desired amino acid sequence, under reaction conditions that will not alter the peptide chain.

The peptides are preferably prepared using solid phase synthesis, such as that described by Merrifield, *J. Am. Chem. Soc.*, 85, p 2149 (1963), although other equivalent chemical syntheses known in the art can also be used as previously mentioned. Solid-phase synthesis is commenced from the C-terminal end of the peptide by coupling a protected α-amino acid to a suitable resin. Such a starting material can be prepared by attaching α-amino-protected Leu or Ala by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London) 38, 1597–98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1–6. BHA and MBHA resin supports are commercially available and are generally used only when the desired polypeptide being synthesized has an α-carboxamide at the C-terminal.

Ala protected by BOC is coupled to the chloromethylated resin according to the procedure of Monahan and Gilon, *Biopolymer* 12, pp 2513–19, 1973. Following the coupling of BOC-Ala to the resin support, the α-amino protecting group is removed, as by using trifluoroacetic acid(TFA) in methylene chloride, TFA alone or HCl in dioxane. The deprotection is carried out at a temperature between about 0° C. and room temperature. Other standard cleaving reagents and conditions for removal of specific α-amino protecting groups may be used as described in Schroder & Lubke, "The Peptides", 1 pp 72–75 (Academic Press 1965).

After removal of the α-amino protecting group of Ala, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are: (1) carbodiimides, such as N,N'-diisopropyl carbodiimide, N-ethyl-N'-(3-dimethylaminopropyl)carbodiimide; (2) cyanamides such as N,N'-dibenzylcyanamide; (3) keteimines; (4) isoxazolium salts, such as N-ethyl-5-phenyl isoxazolium-3'-sulfonate; (5) monocyclic nitrogen-containing heterocyclic amides of aromatic character containing one through four nitrogens in the ring, such as imidazolides, pyrazolides, and 1,2,4-triazolides. Specific heterocyclic amides that are useful include N,N'-carbonyl diimidazole, N,N'-carbonyl-di-1,2,4-triazole; (6) alkoxylated acetylene, such as ethoxyacetylene; (7) reagents which form a mixed anhydride with the carboxyl moiety of the amino acid, such as ethylchloroformate and isobutylchloroformate and (8) reagents which form an active ester with the carboxyl moiety of the amino acid, such as nitrogen-containing heterocyclic compounds having a hydroxy group on one ring nitrogen, e.g. N-hydroxyphthalimide, N-hydroxysuccinimide and 1-hydroxybenzotriazole(HOBT). Other activating reagents and their use in peptide coupling are described by Schroder & Lubke supra, in Chapter III and by Kapoor, *J. Phar. Sci.*, 59, pp 1–27 (1970).

Each protected amino acid or amino acid sequence is introduced into the solid phase reactor in about a two-fold or more excess, and the coupling may be carried out in a medium of dimethylformamide(DMF):$CH_2Cl_2$ (1:1) or in DMF or $CH_2Cl_2$ alone. In cases where incomplete coupling occurred, the coupling procedure is repeated before removal of the α-amino protecting group prior to the coupling of the next amino acid. The success of the coupling reaction at each stage of the synthesis is monitored by the ninhydrin reaction, as described by E. Kaiser et al., *Anal. Biochem.* 34, 595 (1970).

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$, $X^7$ and $X^8$ and the α-amino protecting group $X^1$, to obtain the peptide.

As an alternative route, the intermediate peptide may be separated from the resin support by alcoholysis after which the recovered C-terminal alkyl ester is converted to the acid by hydrolysis. Any side chain protecting groups may then be cleaved as previously described or by other known procedures, such as catalytic reduction (e.g. Pd on $BaSO_4$). When using hydrogen fluoride for cleaving, anisole and methylethyl sulfide are included in the reaction vessel for scavenging.

The following Example sets forth the preferred method for synthesizing PGRF by the solid-phase technique. It will of course be appreciated that the synthesis of a correspondingly shorter peptide fragment is effected in the same manner by merely eliminating the requisite number of amino acids at either end of the chain; however, it is presently felt that biologically active fragments should contain the indicated sequence at the N-terminal.

EXAMPLE I

The synthesis of PGRF(1-44) free acid having the formula:

H—Tyr—Ala—Asp—Ala—Ile—Phe—Thr—Asn—Ser—Tyr—
Arg—Lys—Val—Leu—Gly—Gln—Leu—Ser—Ala—Arg—Lys—
Leu—Leu—Gln—Asp—Ile—Met—Ser—Arg—Gln—Gln—Gly—
Glu—Ser—Asn—Gln—Glu—Arg—Gly—Ala—Arg—Ala—Arg—
Leu—OH is conducted in a stepwise manner using a Beckman 990 Peptide Synthesizer on a chloromethylated resin, such as that available from Lab Systems, Inc., containing 0.9 Meq Cl/g. Coupling of BOC-Leu to the resin is performed by the general procedure set forth by Monahan et al. in *Biopolymers*, Volume 12 (1973) pp. 2513–2519, and it results in the substitution of about 0.22 mmol. Leu per gram of resin. All solvents that are used are carefully degassed by sparging with an inert gas, preferably helium, to insure the absence of oxygen that might undesirably oxidize the sulfur of the Met residue.

After deprotection and neutralization, the peptide chain is built step-by-step on the resin. Deprotection, neutralization and addition of each amino acid is performed in general accordance with the procedure set forth in detail in Guillemin et al. U.S. Pat. No. 3,904,594. The couplings are specifically carried out as set out in the following schedule.

| STEP | SCHEDULE REAGENTS AND OPERATIONS | MIX TIMES MIN. |
|---|---|---|
| 1 | $CH_2Cl_2$ wash (2 times) | 0.5 |
| 2 | 50% trifluoroacetic acid (TFA) + 5% 1,2-ethanedithiol in $CH_2Cl_2$ (1 time) | 0.5 |
| 3 | 50% trifluoroacetic acid (TFA) + 5% 1,2-ethanedithiol in $CH_2Cl_2$ (1 time) | 20.0 |
| 4 | $CH_2Cl_2$ wash (3 times) | 0.5 |
| 5 | $CH_3OH$ wash (2 times) | 0.5 |
| 6 | 10% triethylamine ($Et_3N$) in $CH_2Cl_2$ neutralization (2 times) | 0.5 |
| 7 | $CH_3OH$ wash (2 times) | 0.5 |
| 8 | 10% triethylamine ($Et_3N$) in $CH_2Cl_2$ neutralization (2 times) | 0.5 |
| 9 | $CH_3OH$ wash (2 times) | 0.5 |
| 10 | $CH_2Cl_2$ wash (2 times) | 0.5 |
| 11 | *Boc—amino acid (1 mmole/g resin) plus equivalent amount of dicyclohexylcarbodiimide (DCC) in $CH_2Cl_2$ | 120 |
| 12 | $CH_2Cl_2$ wash (1 time) | 0.5 |
| 13 | 50% dimethylformamide in $CH_2Cl_2$ wash (2 times) | 0.5 |
| 14 | 10% triethylamine ($Et_3N$) in $CH_2Cl_2$ wash (1 time) | 0.5 |
| 15 | $CH_3OH$ wash (2 times) | 0.5 |
| 16 | $CH_2Cl_2$ wash (2 times) | 0.5 |
| 17 | 25% acetic anhydride in $CH_2Cl_2$ (2 ml/g resin) | 20.0 |
| 18 | $CH_2Cl_2$ wash (2 times) | 0.5 |
| 19 | $CH_3OH$ wash (2 times) | 0.5 |

*For the coupling of Asn and Gln, an 1.136 molar excess of 1-hydroxybenzotriazole (HOBt) was included in this step.

Briefly, for the coupling reaction, one mmol. of BOC-protected amino acid in methylene chloride is used per gram of resin, plus one equivalent of 0.5 molar DCCI in methylene chloride or 30% DMF in methylene chloride, for two hours. When Arg is being coupled, a mixture of 10% DMF and methylene chloride is used. Bzl is used as the hydroxyl side-chain protecting group for Ser and Thr. 2-chloro-benzyloxycarbonyl (2Cl—Z) is used as the protecting group for the Lys side chain. Tos is used to protect the guanidino group of Arg, and the Glu or Asp carboxyl group is protected as the Bzl ester. The phenolic hydroxyl group of Tyr is protected with 2,6-dichlorobenzyl. At the end of the synthesis, the following composition is obtained:

$X^1$—Tyr($X^2$)—Ala—Asp($X^3$)—Ala—Ile—Phe—Thr($X^4$)—Asn—
  Ser($X^5$)—Tyr($X^2$)—Arg($X^6$)—Lys($X^7$)—Val—Leu—Gly—Gln—
  Leu—Ser($X^5$)—Ala—Arg($X^6$)—Lys($X^7$)—Leu—Leu—Gln—
  Asp($X^3$)—Ile—Met—Ser($X^5$)—Arg($X^6$)—Gln—Gln—Gly—
  Glu($X^3$)—Ser($X^5$)—Asn—Gln—Glu($X^3$)—Arg($X^6$)—Gly—Ala—
  Arg($X^6$)—Ala—Arg($X^6$)—Leu—$X^8$ wherein $X^1$ is BOC, $X^2$ is 2,6-dichlorobenzyl, $X^3$ is benzyl ester, $X^4$ is Bzl, $X^5$ is Bzl, $X^6$ is Tos, $X^7$ is 2Cl—Z and $X^8$ is —O—CH$_2$-benzene-polystyrene resin support.

After the final Tyr residue has been coupled to the resin, the BOC group is removed with 45% TFA in CH$_2$Cl$_2$. In order to cleave and deprotect the remaining protected peptide-resin, it is treated with 1.5 ml. anisole, 0.25 ml. methylethylsulfide and 10 ml. hydrogen fluoride (HF) per gram of peptide-resin, at −20° C. for one-half hour and at 0.° C. for one-half hour. After elimination of the HF under high vacuum, the resin-peptide remainder is washed alternately with dry diethyl ether and chloroform, and the peptide is then extracted with degassed 2N aqueous acetic acid. Lyophilization of the acetic acid extract provides a white fluffy material.

The cleaved and deprotected peptide is then dissolved in 30% acetic acid and subjected to Sephadex G-50 fine gel filtration.

The peptide is then further purified by CM-32 carboxymethyl cellulose (Whatman) cation-exchange chromatography (1.8×18 cm., $V_{bed}$=50 ml.) using a concave gradient generated by dropping 1 L. of 0.4M NH$_4$OAc, pH 6.5 into a mixing flask containing 400 ml. 0.01M NH$_4$OAc, pH 4.5. Final purification is carried out using partition chromatography on Sephadex G-50 fine support (Pharmacia) with a nBuOH:EtOH:pyridine:0.2% N HOAc (4:1:1:7) solvent system. Purification details are generally set forth in Ling et al. *Biochem. Biophys. Res. Commun.* 95, 945 (1980). The chromatographic fractions are carefully monitored by TLC, and only the fractions showing substantial purity were pooled.

EXAMPLE II

The synthesis of PGRF (1-40) having the formula:

H—Tyr—Ala—Asp—Ala—Ile—Phe—Thr—Asn—Ser—Tyr—
  Arg—Lys—Val—Leu—Gly—Gln—Leu—Ser—Ala—Arg—Lys—
  Leu—Leu—Gln—Asp—Ile—Met—Ser—Arg—Gln—Gln—Gly—
  Glu—Ser—Asn—Gln—Glu—Arg—Gly—Ala—OH is conducted in a stepwise manner using a Beckman 990 Peptide Synthesizer on a chloromethylated resin in the manner described in Example I. The peptide is judged to be substantially pure using TLC and HPLC.

EXAMPLE III

The synthesis of PGRF(1-44)-amide having the formula:

H—Tyr—Ala—Asp—Ala—Ile—Phe—Thr—Asn—Ser—Tyr—
  Arg—Lys—Val—Leu—Gly—Gln—Leu—Ser—Ala—Arg—Lys—
  Leu—Leu—Gln—Asp—Ile—Met—Ser—Arg—Gln—Gln—Gly—
  Glu—Ser—Asn—Gln—Glu—Arg—Gly—Ala—Arg—Ala—Arg—
  Leu—NH$_2$ is conducted in a stepwise manner using a Beckman 990 Peptide Synthesizer on an MBHA resin in the manner described in Example I. This peptide is judged to be substantially pure using TLC and HPLC.

EXAMPLE IV

The synthesis of a PGRF analog having the formula:

H—Tyr—Ala—Asp—Ala—Ile—Phe—Thr—Asn—Ser—Tyr—
  Arg—Lys—Val—Leu—Gly—Gln—Leu—Ser—Ala—Arg—Lys—
  Leu—Leu—Gln—Asp—Ile—Met—Ser—Arg—Gln—Gln—Gly—
  Glu—Ala—Asn—Gln—Glu—Ser—Gly—Arg—OH is conducted in a stepwise manner using a Beckman 990 Peptide Synthesizer on a chloromethylated resin, such as that available from Lab Systems, Inc. in the manner described in Example I. The peptide is judged to be substantially pure using TLC and HPLC.

EXAMPLE V

The synthesis of a PGRF (1-40)-amide having the formula:

H—Tyr—Ala—Asp—Ala—Ile—Phe—Thr—Asn—Ser—Tyr—
  Arg—Lys—Val—Leu—Gly—Gln—Leu—Ser—Ala—Arg—Lys—
  Leu—Leu—Gln—Asp—Ile—Met—Ser—Arg—Gln—Gln—Gly—
  Glu—Ser—Asn—Gln—Glu—Arg—Gly—Ala—NH$_2$ is conducted in a stepwise manner using a Beckman 990 Peptide Synthesizer on an MBHA resin in the manner described in Example I. This peptide is judged to be substantially pure using TLC and HPLC.

EXAMPLE VI

The synthesis of PGRF (1-37)-free acid having the formula:

H—Tyr—Ala—Asp—Ala—Ile—Phe—Thr—Asn—Ser—Tyr—
  Arg—Lys—Val—Leu—Gly—Gln—Leu—Ser—Ala—Arg—Lys—
  Leu—Leu—Gln—Asp—Ile—Met—Ser—Arg—Gln—Gln—Gly—
  Glu—Ser—Asn—Gln—Glu—OH is conducted in a stepwise manner using a Beckman 990 Peptide Synthesizer on a chloromethylated resin in the manner described in Example I. The peptide is judged to be substantially pure using TLC and HPLC.

EXAMPLE VII

To determine the effectiveness of the peptides to promote the release of growth hormone, in vitro assays are carried out using synthetic PGRF (1-40) of Example II in side-by-side comparison with equimolar concentrations of the extracted and purified native PGRF (1-40) and of a GRF Reference Standard having a known effectiveness to promote the release of growth hormone from pituitary cells. The GRF Reference standard is described and defined in Brazeau, et al., *Endocrinology*, Vol. 110, A538(1982) and is an amount of a preparation of rat hypothalamic origin that produces a half-maximal response in terms of GH release in a pituitary cell monolayer bioassay. Cultures are used which include cells of rat pituitary glands removed some four to five days previously. Both cultures of a defined standard medium and cultures which are considered optimal for the secretion of growth hormone are used for the comparative testing, in the general manner described in Brazeau, et al. *Regulatory Peptides*, 1, 255, 1981. Incubation with the substance to be tested is carried out for 3 to 4 hours, and aliquots of the culture medium are removed and processed to measure their contents in inmunoreactive GH(ir GH) by a well-characterized radioimmunoassay.

The results of this comparative testing shows that, in equimolar ratios, the synthetic PGRF (1–40) has the full biological activity of the native peptide, as shown in Table I. The $ED_{50}$ of the synthetic peptide is about 113 picograms, which is far more potent than any other molecule heretofore claimed as a GH releasing factor.

TABLE I

|  | GH secretion in vitro % of controls |
|---|---|
| GRF Reference Standard |  |
| 0.63 unit | 173 ± 0.4 |
| 1.25 units | 230 ± 5 |
| 2.50 units | 347 ± 13 |
| 5.00 units | 474 ± 3 |
| 10.00 units | 674 ± 6 |
| Native PGRF (1-40) |  |
| 12.5 femtomoles | 234 ± 17 |
| 25 fmoles | 351 ± 7 |
| 50 fmoles | 528 ± 16 |
| 100 fmoles | 720 ± 32 |
| 200 fmoles | 748 ± 7 |
| Synthetic PGRF (1-40) |  |
| 10 fmoles | 269 ± 20 |
| 100 fmoles | 701 ± 6 |
| 1000 fmoles | 990 ± 42 |

In addition to the in vitro tests for secretion of growth hormone, in vivo experiments were also run by injecting the synthetic peptide into normal male rats about 200 g. body weight, anesthetized with pentobarbital. The results set forth in TABLE II show that the synthetic PGRF peptide is a powerful stimulator of the secretion of pituitary growth hormone.

TABLE II

In vivo effects of synthetic PGRF (1-40) on the release of pituitary growth hormone following one single intravenous injection in normal rats (4 animals per treatment dose).

Responses in serum ir-GH in nanograms/ml at indicated times before and after injection.

| Doses | −1 min | +5 min | +10 min | +15 min | +30 min | +60 min |
|---|---|---|---|---|---|---|
| 0 microgram | 173 ± 47 | 251 ± 81 | 339 ± 139 | 396 ± 121 | 749 ± 440 | 316 ± 76 |
| 0.01 µg | 173 ± 23 | 284 ± 20 | 238 ± 51 | 201 ± 47 | 261 ± 50 | 299 ± 25 |
| 0.1 µg | 276 ± 126 | 694 ± 246 | 582 ± 290 | 758 ± 562 | 280 ± 70 | 424 ± 129 |
| 1.0 µg | 142 ± 24 | 4551 ± 1825 | 1748 ± 564 | 730 ± 158 | 234 ± 53 | 267 ± 129 |
| 10.0 µg | 234 ± 76 | 7077 ± 1943 | 4676 ± 585 | 2464 ± 378 | 616 ± 112 | 223 ± 26 |

Additional testing shows that synthetic PGRF analog from Example IV exhibits substantially the same biological potency as the native PGRF (1–40) and that the synthetic fragment from Example VI also exhibits very substantial biological potency. Furthermore the PGRF (1–40) peptide having the α-carboxamide at the C-terminal from Example V has substantially twice the biological potency of the synthetic peptide tested in Example VII.

EXAMPLE VIII

The in vitro assays described in Example VII are repeated using Native PGRF(1–40) and Native PGRF(1–44) and the results are set forth in following Table III:

TABLE III

|  | GH secretion in vitro % of controls |
|---|---|
| GRF Reference Standard |  |
| 0.63 unit | 201 ± 2.5 |
| 1.25 units | 305 ± 1.2 |
| 2.50 units | 397 ± 4.7 |
| 5.00 units | 508 ± 7.1 |
| 10.00 units | 583 ± 7.5 |
| Native PGRF (1-40) |  |
| 6.3 femtomoles | 198 ± 5.9 |
| 12.5 femtomoles | 270 ± 2.4 |
| 25.0 femtomoles | 348 ± 3.4 |
| 50.0 femtomoles | 466 ± 0.9 |
| 100.0 femtomoles | 570 ± 17 |
| 200.0 femtomoles | 579 ± 2.1 |
| 400.0 femtomoles | 588 ± 10 |
| Native PGRF (1-44) |  |
| 6.3 femtomoles | 289 ± 10 |
| 12.5 femtomoles | 391 ± 8 |
| 25.0 femtomoles | 479 ± 8 |
| 50.0 femtomoles | 561 ± 14 |
| 100.0 femtomoles | 599 ± 7 |
| 200.0 femtomoles | 606 ± 6 |
| 400.0 femtomoles | 610 ± 5 |

Potency:
(a) in terms of GRF Reference Standard: 1 femtomole PGRF(1–44)=0.1696 unit, with confidence limits of 0.122 and 0.239
(b) in terms of PGRF(1–40): PGRF(1–44)=2.2261×PGRF(1–40), with confidence limits of 1.616 and 3.131.

Potencies were computer calculated using program BIOPROG.

Further testing shows that synthetic PGRF(1–44)-free acid as synthesized in Example I exhibits somewhat less potency than native PGRF(1–44) and that synthetic PGRF(1–44)-amide exhibits substantially the same potency as native PGRF(1–44). Synthetic PGRF (1–44)-amide, when injected in laboratory animals(rats), shows the same type of GH-releasing activity as PGRF(1–40) as demonstrated in Table II of Example VII.

Approximately 1 out of 7000 to 15,000 children born in the USA are known to be pituitary growth hormone deficient or "pituitary-dwarfs", i.e., they are dwarfs because they lack the normal levels of pituitary GH in their blood. There are clinical reasons to propose that most of these patients have a normal pituitary gland and that the cause of their problem is a lack either of the synthesis, or of the secretion, of the hypothalamic releasing factor for GH. Synthetic PGRF is expected to be the ideal treatment for these cases who have heretofore been treated by injections of human pituitary GH, an extremely expensive preparation obtained exclusively from human pituitaries at autopsies. Human GH prepared by DNA-recombinant methodology, though announced in the literature, is not currently available for routine use. Synthetic PGRF is a far simpler molecule and should have significant advantages for use throughout the world where the number of such pituitary dwarfs is estimated to be several hundreds of thousands.

Because synthetic PGRF is the first known molecule specifically to assess the pituitary function in terms of GH secretion, it thus represents the first routine test for GH secretion in all cases in which a specific defect of pituitary function is suspected by a physician. Synthetic PGRF should henceforth replace the cumbersome methods used currently (arginine infusions, hypoglycemia, L-DOPA injections, etc.) to assess GH secretory ability as a diagnostic procedure.

Synthetic PGRF should be of interest in all cases in clinical medicine in which a physician wishes to favor a positive nitrogen balance and anabolism, such as wound-healing, treatment of extensive burns, post-operative periods following extensive surgery and other medical situations of debilitation, including many syndromes of gerontological practice as well as of the pediatric practice of prematurely born infants. Stimulation of GH secretion is of interest in patients during and after extensive radiation therapy for solid tumors, again to promote anabolism and also to take advantage of the effects of GH on the stimulation of the stem cells of the hematopoietic system. For administration to humans, synthetic PGRF peptides should have a purity of at least about 93% and preferably at least 98%. This purity means the intended peptide constitutes the stated weight % of all like peptides and peptide fragments present.

Most of the biologically active peptides have been found to possess biological activities other than those for which they were originally recognized. In view of such precedents, it is likely that PGRF will be found to possess extrapituitary activities which may be of practical interest. Although PGRF was extracted and isolated from a human pancreatic tumor, on the basis of overall experience and experimentation, it is believed the amino acid sequence of PGRF(1-44)-amide is the same as the sequence of human hypothalamic GH releasing factor.

Chronic administration of synthetic PGRF peptides to farm animals is expected to promote anabolism and thus increase body weight in terms of muscle mass. Administration to animals at a purity as low as about 5% may be acceptable.

Synthetic PGRF or the nontoxic salts thereof, combined with a pharmaceutically acceptable carrier to form a pharmaceutical composition, may be administered to mammals, including humans, either intravenously, subcutaneously, intramuscularly or orally. The administration may be employed by a physician to stimulate the release of growth hormone where the host being treated requires such therapeutic treatment. The required dosage will vary with the particular condition being treated, with the severity of the condition and with the duration of desired treatment.

Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically-acceptable carrier. Usually, the dosage will be from about 20 to about 2000 nanograms of the peptide per kilogram of the body weight of the host.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, modifications in the 44-member chain, particularly deletions beginning at the carboxyl terminal of the peptide, can be made in accordance with the known experimental practises to date to create fragments that retain all or very substantial portions of the potency of the peptide, and such peptides are considered as being within the scope of the invention. Moreover, additions can be made to either terminal, or to both terminals, and/or generally equivalent residues can be substituted for naturally occurring residues, as is well-known in the overall art of peptide chemistry to produce analogs having at least a substantial portion of the potency of the native polypeptide without deviating from the scope of the invention.

Various features of the invention are emphasized in the claims which follow.

What is claimed is:

1. A synthetic peptide having the formula:

H—Tyr—Ala—Asp—Ala—Ile—Phe—Thr—Asn—Ser—Tyr—
Arg—Lys—Val—Leu—Gly—Gln—Leu—Ser—Ala—Arg—Lys—
Leu—Leu—Gln—Asp—Ile—Met—Ser—Arg—Gln—Gln—Gly—
Glu—$R_{34}$—Asn—Gln—Glu—$R_{38}$—Gly—$R_{40}$—$R_{41}$—R wherein R is OH or $NH_2$, $R_{34}$ is Ser or Ala, $R_{38}$ is Arg or Ser, $R_{40}$ is Ala or Arg and $R_{41}$ is Arg, Arg-Ala, Arg-Ala-Arg or Arg-Ala-Arg-Leu, or a fragment of such peptide which fragment is biologically active to effect the release of GH, or a nontoxic salt of such peptide or peptide fragment.

2. A synthetic peptide having the formula of claim 1 wherein $R_{34}$ is Ser, $R_{38}$ is Arg and $R_{40}$ is Ala.

3. A synthetic peptide having the formula of claim 2 wherein $R_{41}$ is Arg-Ala-Arg-Leu.

4. A synthetic peptide having the formula of claim 3 wherein R is $NH_2$.

5. A synthetic peptide having the formula of claim 3 wherein R is OH.

6. A method of stimulating the release of GH in mammals by administering an effective amount of a synthetic peptide as defined in claim 1.

7. A method of improving muscle mass in nonhuman animals by administering an amount of a compound as defined in claim 1 which is effective to accelerate anabolism.

8. A pharmaceutical composition comprising a synthetic peptide as defined in claim 1 in an amount effective to stimulate the release of GH in a human and a pharmaceutically acceptable liquid or solid carrier therefor.

9. A method of stimulating the release of growth hormone in an animal, which comprises administering an effective amount of a synthetic peptide having the sequence:

Tyr—Ala—Asp—Ala—Ile—Phe—Thr—Asn—Ser—Tyr—
Arg—Lys—Val—Leu—Gly—Gln—Leu—Ser—Ala—Arg—Lys—
Leu—Leu—Gln—Asp—Ile—Met—Ser—Arg—Gln—Gln—Gly—
Glu—Ser—Asn—Gln—Glu—Arg—Gly—Ala—$R_{41}$ wherein
$R_{41}$ is Arg, Arg—Ala, Arg—Ala—Arg or Arg—Ala—Arg—Leu, or a fragment of such peptide which fragment is biologically active to effect the release of GH by the pituitary, or a nontoxic salt of such peptide or peptide fragment.

10. A method in accordance with claim 9 for stimulating the release of GH in nonhuman animals.

11. A method of improving growth in farm animals in accordance with claim 10 by administering an amount effective to accelerate anabolism.

12. A method in accordance with claim 9 wherein the carboxyl terminus is free acid or amide.

13. A method for stimulating the release of GH in a human in accordance with claim 10 by administering said effective amount in combination with a pharmaceutically acceptable liquid or solid carrier therefor.

14. A method in accordance with claim 1 wherein said synthetic peptide is a biologically active fragment of the 40-residue peptide including the N-terminal sequence thereof.

15. A method in accordance with claim 14 wherein the carboxyl terminus is free acid.

16. A method in accordance with claim 14 wherein the carboxyl terminus is amide.

17. A pharmaceutical composition comprising an effective amount of a synthetic peptide having the sequence:

Tyr—Ala—Asp—Ala—Ile—Phe—Thr—Asn—Ser—Tyr—
Arg—Lys—Val—Leu—Gly—Gln—Leu—Ser—Ala—Arg—Lys—
Leu—Leu—Gln—Asp—Ile—Met—Ser—Arg—Gln—Gln—Gly—
Glu—Ser—Asn—Gln—Glu—Arg—Gly—Ala—$R_{41}$ wherein and $R_{41}$ is Arg, Arg-Ala, Arg-Ala-Arg or Arg-Ala-Arg-Leu, or a fragment of such peptide which fragment is biologically active to effect the release of GH by the pituitary, or a nontoxic salt of such peptide or peptide fragment, plus an acceptable nontoxic liquid or solid carrier therefor, said amount being effective to stimulate the release of GH.

18. A composition in accordance with claim 17 wherein $R_{41}$ is Arg-Ala-Arg-Leu.

19. A composition in accordance with claim 18 wherein the carboxyl terminus is amide.

20. A composition in accordance with claim 18 wherein the carboxyl terminus is free acid.

* * * * *

UNITED STATES PATENT AND TRADEMARK OFFICE
CERTIFICATE OF CORRECTION

PATENT NO. : 4,517,181

DATED : May 14, 1985

INVENTOR(S) : Nicholas C. Ling et al.

It is certified that error appears in the above-identified patent and that said Letters Patent is hereby corrected as shown below:

Column 13, line 32, change "10" to --9--.

Column 14, line 3, change "1" to --9--.

Signed and Sealed this

Fifteenth Day of October 1985

[SEAL]

Attest:

DONALD J. QUIGG

Attesting Officer

Commissioner of Patents and Trademarks—Designate